United States Patent [19]

Hersch et al.

[11] Patent Number: 5,958,449
[45] Date of Patent: *Sep. 28, 1999

[54] ANTIBIOTIC FORMULATION AND USE FOR BACTERIAL INFECTIONS

[75] Inventors: Evan M. Hersch; Eskild A. Petersen, both of Tucson, Ariz.; Richard T. Proffitt, Arcadia, Calif.; Kevin R. Bracken, Sunland, Calif.; Su-Ming Chiang, Canoga Park, Calif.

[73] Assignee: NeXstar Pharmaceuticals, Inc., Boulder, Colo.

[*] Notice: This patent is subject to a terminal disclaimer.

[21] Appl. No.: 09/082,633

[22] Filed: May 21, 1998

Related U.S. Application Data

[63] Continuation of application No. 08/084,218, filed as application No. PCT/US93/04501, May 11, 1993, Pat. No. 5,759,571, which is a continuation-in-part of application No. PCT/US92/10591, Dec. 2, 1992.

[51] Int. Cl.$^6$ ............................ A61K 9/127; A61K 9/133
[52] U.S. Cl. ............................................. 424/450; 264/4.3
[58] Field of Search ............................ 424/450; 264/4.1, 264/4.3, 4.6

[56] References Cited

U.S. PATENT DOCUMENTS

| | | |
|---|---|---|
| 4,508,703 | 4/1985 | Redziniak et al. |
| 4,522,803 | 6/1985 | Lenk et al. |
| 4,621,023 | 11/1986 | Redziniak et al. |
| 4,753,788 | 6/1988 | Gamble |
| 4,762,720 | 8/1988 | Jizomoto et al. |
| 4,897,384 | 1/1990 | Janoff et al. |
| 4,933,121 | 6/1990 | Law ................................ 264/4.3 |
| 4,946,683 | 8/1990 | Forssen |
| 4,952,405 | 8/1990 | Young ............................ 424/423 |
| 4,981,692 | 1/1991 | Popescu et al. |
| 5,000,887 | 3/1991 | Teuzel ............................ 424/450 |
| 5,023,087 | 6/1991 | Yau-Young |
| 5,043,107 | 8/1991 | Adler-Moore et al. |
| 5,043,165 | 8/1991 | Radhakrishnam ............. 424/450 |
| 5,053,217 | 10/1991 | Lehigh |
| 5,211,955 | 5/1993 | Legros et al. |
| 5,270,052 | 12/1993 | Gelfand et al. |
| 5,376,452 | 12/1994 | Hope et al. |
| 5,409,704 | 4/1995 | Bally ............................... 424/450 |
| 5,756,120 | 5/1998 | Hersch ............................ 424/450 |
| 5,756,121 | 5/1998 | Bracken ......................... 424/450 |
| 5,759,571 | 6/1998 | Hersch ............................ 424/450 |

FOREIGN PATENT DOCUMENTS

| | | |
|---|---|---|
| 0 087 993 B2 | 2/1983 | European Pat. Off. |
| 0 295 248 B1 | 12/1988 | European Pat. Off. |
| 0 394 265 B1 | 10/1990 | European Pat. Off. |
| 0 500 143 A2 | 8/1992 | European Pat. Off. |
| 0 565 361 B1 | 10/1993 | European Pat. Off. |
| 5 7082-31 | 5/1982 | Japan. |
| 85/00515 | 2/1985 | WIPO. |
| 85/00751 | 2/1985 | WIPO. |
| 88/04573 | 6/1988 | WIPO. |
| 93/23015 | 11/1993 | WIPO. |

OTHER PUBLICATIONS

Bakker–Woudenbert et al. (1995) J. Infect. Dis. 171:938.
Barza et al. (1984) Investigative Ophthalmology & Visual Science 25:486.
Bermudez et al (1990) J. Infect. Dis. 161:1262.
Bermudez et al. (1987) J. Infect. Dis. 156:510.
Bonventre & Gregoriadis (1978) Antimicrobial Agents and Chemotherapy 13:1049.
Dees et al. (1985) Veterinary Immunology and Immunopathology 8:171.
Duzgunes, et al. (1988) Antimicrobial Agents and Chemotherapy, 32:1404.
Duzgunes et al. (1991) J. Infect. Dis. 164:143.
Fishman et al. (1986) Investigative Ophthalmology and Visual Science 27:1103.
Fountain et al. (1981) Current Microbiology 6:373.
Fountain et al. (1980) Biochimica et Biophysica Acta 596:420.
Gangadharam et al. (1989) Liposomes in the Therapy of Infectious Diseases and Cancer, pp. 177–190.
Karlowsky and Zhanel (1992) Clinical Infect. Dis. 15:654.
Kubo et al. (1986) Biochemical Pharmacology 35:3761.
Majumdar et al. (1992) Antimicrobial Agents and Chemotherapy 36:2808.
Saito and Tomioka (1989) Antimicrobial Agents & Chemotherapy 33:429.
Schreier et al. (1987) J. Controlled Release 5:187.
Stevenson et al. (1983) Antimicrobial Agents & Chemotherapy 24:742.
Tadakuma et al. (1985) Antimicrobial Agents & Chemotherapy 28:28.
Wichert et al. (1992) Int. J. Pharm. 78:227.

*Primary Examiner*—Gollamudi S. Kishore
*Attorney, Agent, or Firm*—Swanson & Bratschun LLC

[57] ABSTRACT

A liposomal aminoglycoside formulation comprising a neutral lipid, a negatively charged lipid and a sterol. The formulation contains unilamellar vesicles having an average size below 100 nm. A process of making liposomes containing an aminoglycoside is provided. A method is also provide for the treatment of drug susceptible and drug resistant bacteria.

26 Claims, No Drawings

ANTIBIOTIC FORMULATION AND USE FOR BACTERIAL INFECTIONS

This is a Continuation of U.S. patent application Ser. No. 08/084,218, now U.S. Pat. No. 5,759,571, which is a 35 USC §371 filing of PCT/US93/04501, filed May 11, 1993, which is a Continuation-in-Part application of PCT/US92/10591, filed Dec. 2, 1992.

FIELD OF THE INVENTION

This invention relates to the fields of biochemistry and medicine, and particularly to a liposome formulation. More specifically, it relates to a liposomal formulation containing an aminoglycoside, its process of manufacture and its use. This invention also relates to formulations having reduced toxicity, longer stability, and superior efficacy. This invention further relates to liposomal formulations containing amikacin and its use in treating drug susceptible and drug resistant strains of bacterial infections.

BACKGROUND OF THE INVENTION

The discovery of aminoglycosides began in the 1940s with the isolation of streptomycin from *Streptomyces griseus*. Since the 1940s, other aminoglycosides have been discovered and synthesized. These include neomycin which is obtained or isolated from *Streptomyces fradiae*; kanamycin which is isolated from *Streptomyces kanamyceticus*; gentamicin which is isolated from *Micromonospora purpurea*; tobramycin which is isolated from *Streptomyces tenedrarius*; sisomicin isolated from *micromonospora inyoesis*; amikacin which is a semisynthetic derivative of Kanamycin A; and netilmicin which is a semisynthetic derivative of sisomicin. Amikacin has the broadest spectrum of antimicrobial activity of all the aminoglycosides. It also has a unique resistance to the immunoglycoside-inactivating enzymes.

The aminoglycosides are polar-cations which consist of two or more amino sugars joined in a glycosidic linkage to a hexose nucleus, which is usually in a central position. The aminoglycosides are used primarily to treat infections caused by gram-negative bacteria. However, aminoglycosides have been used in recent years to treat bacteria from the *genus Mycobacterium*. For example, amikacin has shown to be effective against *Mycobacterium tuberculosis*. Aminoglycosides have also been tested against *M.avium* infections including *M. avium-intracellulare* complex (MAC) which is a group of related acid-fast organisms that grow only slightly faster than *M. tuberculosis* and can be divided into a number of serotypes. At the beginning of the twentieth century, tuberculosis was the most prevalent cause of death in the United States. By the late 1940s, with the advent of streptomycin, tuberculosis infection had decreased substantially. Since the mid-1980s with the appearance of the acquired immune deficiency syndrome, tuberculosis again began to emerge as a major health problem. Further, the new cases of tuberculosis showed resistance to many of the available antibiotic therapies. Similarly MAC, once considered rare, is now the most common systemic bacterial type infections in patients suffering from acquired immune deficiency syndrome. Hence, the search for an effective antibiotic has intensified.

Although the aminoglycosides have been useful in treating infections, the use of these antibiotics is not free from toxicity and side effects. Aminoglycosides may produce irreversible vestibular, cochlear, and renal toxicity. The two main toxic effects of aminoglycosides are ototoxicity and nephrotoxicity. Studies have found that the aminoglycosides antibiotics may cause polyuria, decreased urinary osmolality, proteinuria, enzymuria, glycosuria, and a decrease in the rate of glomerular filtration. Some investigators believe that nephrotoxicity results from the accumulation of the aminoglycosides in the renal cortex because of the long half-life of the agents in that tissue.

Liposomes are microscopic vesicles made, in part, from phospholipids which form closed, fluid filled spheres when dispersed with water. Phospholipid molecules are polar, having a hydrophilic ionizable head and two hydrophobic tails consisting of long fatty acid chains. Thus, when sufficient phospholipid molecules are present with water, the tails spontaneously associate to exclude water while the hydrophilic phosphate heads interact with water. The result is a bilayer membrane in which the fatty acid tails converge in the newly formed membrane's interior and the polar heads point in opposite directions toward an aqueous medium. These bilayer membranes can be caused to form closed spheres known as liposomes. The polar heads at the inner surface of the membrane point toward the aqueous interior of the liposome. At the opposite surface of the spherical membrane, the polar heads interact with the surrounding aqueous medium. As the liposomes are formed, water soluble molecules can be incorporated into the aqueous interior, and lipophilic molecules will tend to be incorporated into the lipid bilayer. Liposomes may be either multilamellar, like an onion with liquid separating many lipid bilayers, or unilamellar, with a single bilayer surrounding an entirely liquid center.

There are many types of liposome preparation techniques which may be employed and which produce various types of liposomes. These can be selected depending on the use, the chemical intended to be entrapped, and the type of lipids used to form the bilayer membrane. The requirements which must be considered in producing a liposome preparation are similar to those of other controlled release mechanisms. They are as follows: (1) high percent of chemical entrapment; (2) increased chemical stability; (3) low chemical toxicity; (4) rapid method of production; and (5) reproducible size distribution.

The first method described to encapsulate chemicals in liposomes involved production of multilamellar vesicles (MLVs). Methods for encapsulating chemicals in MLVs are known in the art.

Liposomes can also be formed as unilamellar vesicles (UVs), which generally have a size less than 1 $\mu$m. There are several techniques known in the art which are used to produce unilamellar liposomes.

Smaller unilamellar vesicles can be formed using a variety of techniques. By dissolving phospholipids in ethanol and injecting them into a buffer, the lipids will spontaneously rearrange into unilamellar vesicles. This provides a simple method to produce UVs which have internal volumes similar to that of those produced by sonication (0.2–0.5 L/mol/lipid). Sonication or extrusion (through filters) of MLVs also results in dispersions of UVs having diameters of up to 0.2 $\mu$m, which appear as clear or translucent suspensions.

Another common method for producing small UVs is the detergent removal technique. Phospholipids are solubilized in either ionic or non-ionic detergents such as cholates, Triton X, or n-alkylglucosides. The drug is then mixed with the solubilized lipid-detergent micelles. Detergent is then removed by one of several techniques: dialysis, gel filtration, affinity chromatography, centrifugation, ultrafiltration. The size distribution and entrapment efficiencies of the UVs produced this way will vary depending on the details of the technique used.

The therapeutic use of liposomes includes the delivery of drugs which are normally toxic in the free form. In the liposomal form the toxic drug may be directed away from the sensitive tissue and targeted to selected areas. Liposomes can also be used therapeutically to release drugs, over a prolonged period of time, reducing the frequency of administration. In addition, liposomes can provide a method for forming an aqueous dispersion of hydrophobic drugs for intravenous delivery.

When liposomes are used to target encapsulated drugs to selected host tissues, and away from sensitive tissues, several techniques can be employed. These procedures involve manipulating the size of the liposomes, their net surface charge as well as the route of administration. More specific manipulations have included labeling the liposomes with receptors or antibodies for particular sites in the body.

The route of delivery of liposomes can also affect their distribution in the body. Passive delivery of liposomes involves the use of various routes of administration, e.g., intravenous, subcutaneous and topical. Each route produces differences in localization of the liposomes. Two common methods used to actively direct the liposomes to selected target areas are binding either antibodies or specific receptor ligands to the surface of the liposomes. Antibodies are known to have a high specificity for their corresponding antigen and have been shown to be capable of being bound to the surface of liposomes, thus increasing the target specificity of the liposome encapsulated drug.

Since the chemical composition of many drugs precludes their intravenous administration, liposomes can be very useful in adapting these drugs for intravenous delivery. Many hydrophobic drugs, including cyclosporine, fall into this category because they cannot be easily dissolved in a water-based medium and must be dissolved in alcohols or surfactants which have been shown to cause toxic reactions in vivo. Liposomes, composed of lipids, with or without cholesterol, are nontoxic. Furthermore, since liposomes are made up of amphipathic molecules, they can entrap hydrophilic drugs in their interior space and hydrophobic molecules in their lipid bilayer. Although methods for making liposomes are well known in the art, it is not always possible to determine a working formulation without undue experimentation.

Liposomal formulations containing aminoglycosides have been prepared. Many of the preparations include aerosol formulations using MLVs. Other formulations contain a large amount of negatively charged lipids, generally greater than 20%, to increase retention time or circulation half-life. Problems associated with aminoglycosides liposomal formulations include short retention time in the system because of RES uptake. Attempted formulations in the art have also resulted in liposomal aminoglycosides that are unstable—both on the shelf and in serum.

Thus, it is a desideratum to provide for a novel formulation which would increase the retention time of an aminoglycoside in a mammal's system and which can deliver more drug with superior efficacy and lower toxicity than free drug. It is also desirable to provide a process which allows the manufacture of a clear, stable and efficacious aminoglycoside liposome suspension because of the inability of those of ordinary skill to produce a therapeutically effective aminoglycoside unilamellar liposomal formulation having an average particle size of less than 100 nm, preferably with a high drug to total lipid ratio.

SUMMARY OF THE INVENTION

Liposomes are provided in the present invention which comprise an aminoglycoside wherein the liposomes are unilamellar having an average size of 100 nm or less. A liposomal formulation is provided which comprises an aminoglycoside wherein the liposomes are comprised of a neutral lipid, a sterol and a negatively charged lipid. Small unilamellar vesicles are also provided wherein the molar amount of negatively charged lipid is less than 20% of total lipid. A preferred formulation is liposomes having an aminoglycoside wherein the liposomes are unilamellar vesicles having an average size of 30 nm to 100 nm and further comprised of a phosphatidylcholine, cholesterol, and a phosphatidylglycerol wherein the molar amount of phosphatidylglycerol is less than 5% and preferably about 3%. The drug to total lipid ratio is between 1:9 and 1:3 with the preferred ratio at about 1:4. A preferred formulation is also provided comprising liposomes including an aminoglycoside wherein the liposomes are unilamellar vesicles having an average size less than 100 nm wherein the lipids comprise hydrogenated soy phosphatidylcholine, cholesterol, and distearoylphosphatidylglycerol in a molar ratio of about 2:1:0.1.

The present invention also includes a method for making aminoglycoside liposomes. The process comprises forming a lipid powder comprised of a neutral phospholipid, a sterol, and a negatively charged lipid; mixing the powder with an aminoglycoside in an aqueous buffer and hydrating the mixture at a temperature significantly below the transition temperature of the lipid mixture; and reducing the size of the liposome to an average particle size of less than 100 nm.

The present invention also provides for the treatment of bacterial infections in mammals comprising preparing a liposomal formulation having an aminoglycoside wherein the liposomes are those described above and which are used to treat infections by introducing a therapeutic effective amount of the liposomes into a mammal. Thus, the present invention provides the use of liposomal aminoglycoside formulations to treat bacterial infections. The bacterial infections treated include opportunistic aerobic gram-negative bacilli such as the genera Pseudomonas. Another aspect of the invention includes the use of the liposomal formulations in the treatment of a bacterial infection caused by *P. aeruginosa*. The method of treating bacterial infections is not limited to gram-negative infections. The liposomal formulations can be used to treat bacterial infections comprising gram-positive bacilli such as the *genus Mycobacterium*. The invention is particularly useful for treating mycobacteria which causes tuberculosis-like diseases. Numerous bacterium may be treated using the liposomes described above. The bacteria would include: *M. tuberculosis, M. leprae, M. Intracellulare, M. smegmatis, M. bovis, M. kansasii, M. avium, M. scrofulcium, or M. africanum*. Liposomal formulations of aminoglycoside are also particularly useful in treating MAC.

A particularly useful aspect of the invention is a method of treating a drug resistant bacterial infection in a patient, comprising the delivery to the patient an effective amount of liposomes comprising an encapsulated aminoglycoside wherein the liposomes are comprised of unilamellar vesicles comprised of a neutral lipid, cholesterol and a negatively charged lipid, and having an average size of less than 100 nm. Experiments performed in vitro establish that liposomal amikacin inhibits and kills drug resistant *M. tuberculosis*. The experiments performed further establish that liposomal amikacin kills *M. tuberculosis*, whereas the free drug, at equivalent dosage concentration, only inhibits the growth of the bacteria. Killing is defined as a reduction in the number of colony forming units of bacteria from a previous time point. Inhibition is defined as an increase in, or the same number of, colony forming units of bacteria from a previous time point but less than the number of colony forming units shown for untreated cultures at the same time points. Thus, the present invention provides for the killing of the bacteria at tolerable non-toxic levels in cases where the bacteria is resistant to aminoglycosides and other antibiotics or where the free drug has at the most an inhibitory effect.

The present invention also shows that liposomal amikacin is retained in blood plasma significantly longer than free amikacin. Intermittent treatment of non-compliant patients is obtained in the present invention as the present invention provides higher peak serum levels, prolonged serum half life and increased uptake and retention by macrophages.

The present invention also provides a method for the treatment of drug susceptible *M. tuberculosis* by delivering an effective amount of liposomal amikacin to a patient wherein the dosage levels provide inhibition or killing at levels equivalent to or greater than free amikacin. Thus advantages provided by the decreased toxicity and increased serum levels of amikacin delivered by liposomal amikacin provide a preferable and useful alternative to treatment provided by the free (unencapsulated) amikacin.

Many, if not all, mycobacteria infections discussed above are difficult to treat because the bacteria invade phagocytic cells such as macrophages. Application of liposomal formulations containing an aminoglycoside result in the intracellular delivery of the drug which would not normally occur with the delivery of the free drug. Thus, the present invention provides a treatment of infected phagocytic cells in mammals by delivering a therapeutic or effective amount of an aminoglycoside into a macrophage using a unilamellar liposome having an average size of 100 nm or less.

Provided herein is a liposomal amikacin formulation which can be delivered to a mammal and which provides the following benefits over free amikacin: 1) significantly higher doses of amikacin delivered to sites of infection; 2) substantially lower toxicity; and 3) retention in blood plasma for a significantly longer period of time.

DETAILED DESCRIPTION OF THE INVENTION

As used herein, the term liposome refers to unilamellar vesicles or multilamellar vesicles such as described in U.S. Pat. Nos. 4,753,788 and 4,935,171, the contents of which are incorporated herein by reference.

The present invention provides liposomal aminoglycoside formulation preferably containing a neutral lipid such as a phosphatidylcholine, a phosphatidylglycerol, cholesterol (CHOL) and amikacin. Preferred lipid include lipids which are chemically pure and/or are fully saturated. The preferred neutral lipids are saturated lipids such as hydrogenated egg phosphatidylcholine (HEPC), hydrogenated soy phosphatidylcholine (HSPC), distearoyl phosphatidylcholine (DSPC), and dipalmitoyl phosphatidylcholine (DPPC). The preferred carbon chain lengths of the neutral lipids are from $C_{16}$–$C_{18}$. The preferred negatively charged lipids are saturated lipids such as hydrogenated soy phosphatdylglycerol (HSPG), hydrogenated egg phosphatidylglycerol (HEPG), distearyolphosphatidylglycerol (DSPG), dimyristoylphosphatidylcholine. Hydrogenated soy phosphatidylcholine (HSPC), distearoylphosphatidylglycerol (DSPG) are the preferred lipids for use in the invention. Other suitable phosphatidylcholines include those obtained from egg or plant sources, or those that are partially or wholly synthetic. Other phosphatidylglycerols that may be used are saturated semisynthic lipids having carbon chain lengths from $C_{12}$–$C_{18}$ and include dimyristoyl phosphatidylglycerol (DMPG) and dilaurylphosphatidylglycerol (DLPG).

The preferred formulation includes liposomes comprising an encapsulated aminoglycoside wherein the liposomes are unilamellar vesicles having an average size of less than 100 nm and which are stable for at least two weeks at 22° C. without a significant change in size or without loss of more than 10% of encapsulated aminoglycosides. Generally the size of the liposomes would not vary by more than 30% and most preferably would not vary by more than 20%. The preferred ratio of HSPC:CHOL:DSPG is about 2:1:0.1 and the drug to total lipid ratio is about 1:4. Other preferred formulations include DSPG in a molar amount of 0 to 20% and most preferably in a molar amount of less than 5%. Other preferred formulations include formulations where the drug to total lipid ratio is from 1:9 to 1:3.

The process of the present invention is initiated with the preparation of a solution from which the liposomes are formed. A quantity of a phosphatidylcholine, a phosphatidylglycerol and cholesterol is dissolved in an organic solvent, preferably a mixture a 1:1 (by volume) mixture of chloroform and methanol, to form a clear solution. Other solvents (and mixture thereof), such as ether, ethanol and other alcohols can be used. The preferred temperature to dissolve the lipids is between room temperature and 60° C., preferably at room temperature. The solution is evaporated to form a lipid film or a lipid powder. To form a lipid film, the solvents are evaporated under nitrogen between room temperature and 60° C., preferably at room temperature. To form a lipid powder, the mixture of lipids in solution as described above is sprayed in a spray drier. Preferably, the spraying takes place under nitrogen.

An aminoglycoside, for example, amikacin free base, is dissolved in an aqueous phosphate buffer with 9% sucrose and the pH is adjusted between 6 and 8, preferably between 6 and 7.5 and most preferably between 6.2 and 6.6. The preferred pH is about 6.4. The buffer may also be adjusted to a pH of about 7.4. The pH of the buffer is adjusted with diluted acids and bases preferably with 6N HCl and 2.5N NaOH. The preferred buffer is 10 mM phosphate buffer. However, other aqueous buffers can be used such as succinate buffer (Disodium succinate hexahydrate). The aminoglycoside solution is mixed with either the lipid film or the lipid powder and hydrated, preferably between 40° C. and 65° C. most preferably between 45° C. and 65° C. The solution should be hydrated for at least ten minutes.

Unilamellar vesicles are formed by the application of a shearing force to the hydrated solution, e.g., by extrusion, sonication, or the use of a homogenizing apparatus such as a Gaulin homogenizer or a French press. Shearing force can also be applied using injection, freezing and thawing, dialyzing away a detergent solution from lipids, or other known methods used to prepare liposomes. The size of the liposomes can be controlled using a variety of known techniques including the duration of shearing force. Preferably, the modified Gaulin homogenizing apparatus described in U.S. Pat. No. 4,753,788 is employed to form unilamellar vesicles having diameters of less than 100 nm at a pressure of 7,000 to 13,000 psi and a temperature significantly below the transition temperature of the lipids.

The above described formulations are particularly useful for the treatment of MAC and *Pseudomonas aeruginosa* infections. The use of the above formulations indicate that MAC may be treated with significantly more amikacin delivered in a liposomal formulation than with free drug. For example it has been shown that up to 320 mg of amikacin per kilogram of mice body-weight which is more than 50% more than is tolerated with free drug. The use of the above formulations also indicates that a liposomal formulation is able to deliver significantly more amikacin to a mammal than free drug in the treatment of P. aeruginosa.

Amikacin delivered through a liposomal formulation is also retained in the plasma longer than free amikacin.

The above described formulations are also efficacious in inhibiting and killing both drug resistant and drug susceptible M. tuberculosis as established by in vitro testing. In one experiment the drug resistant strain Vertulla of M. tuberculosis was tested. In another experiment the drug susceptible strain H37RV was tested. The experiments were carried out as described in Example 6. Briefly, human monocytes derived macrophage cultures were developed and infected with either the drug resistant strain or the drug susceptible strain. Liposomal amikacin was prepared as described in Example 1 below. The liposomes comprised HSPC, cholesterol and DMPG in a molar ration of about 2:1:0.1. The drug to total lipid ratio was 1:4 (about 25%). The average size of the liposomes was under 100 nm.

In the experiment performed on the susceptible strain, liposomal and free amikacin were added to the cultures at the following concentrations (μg/ml): 1, 2, and 4. Untreated cultures and cultures treated with liposomes-only were used as controls. The cultures were assayed at 0, 4, and 7 days after infection. The 1 μg/ml concentrations of both the free amikacin and the liposomal amikacin inhibited the growth of the bacteria with the liposomal amikacin showing greater inhibition and also killing at day 4. The 2 μg/ml concentrations of both the free amikacin and the liposomal amikacin were also effective in treating the infection wherein the liposomal amikacin obtained killing at day 4 and the free drug obtained inhibition. The 4 μg/ml concentrations of both the liposomal and the free amikacin obtained killing at day 4 with the liposomal amikacin showing greater killing. Thus, liposomal amikacin provides a preferred treatment of *M. tuberculosis* because the present invention provides, at the least, equivalent inhibition and killing at similar concentrations than free amikacin with lower toxicity and longer plasma retention time.

In the experiment performed on the resistant strain, liposomal and free amikacin were added to the cultures at the following concentrations (μg/ml): 4, 8, and 16. Untreated cultures and cultures treated with liposomes-only were used as controls. The cultures were assayed at 0, 4, and 7 days after infection. At day 4 the liposomal amikacin achieved a bacterial growth of a least twenty-one-fold, sixty-four-fold and several hundred-fold (e.g. 563×) less than the untreated control for the 4 μg/ml, 8 μg/ml and 16 μg/ml concentration, respectively. This activity was 8.7, 12.9 and 130 times more effective than for the respective free amikacin concentrations.

At day 7 the liposomal amikacin achieved bacterial growth of at least one-hundred-fold, (e.g. 133×), one-thousand-fold (e.g. 1110×) and several thousand-fold (e.g. 5880×) less than the untreated control. This activity was 41, 11.9 and 46 times more effective than for the respective amikacin concentrations.

The results show that free amikacin would only inhibit the growth of the infection without killing at the concentrations tested. The liposomal amikacin provided killing of the drug resistant bacteria at all concentrations at day 4. Thus, liposomal amikacin provided high degree of killing where only an inhibitory effect was expected against the drug resistant strain.

Since dosage regimens for aminoglycosides are well known to medical practitioners, the amount of the liposomal aminoglycoside formulation which is effective for the treatment of infections in mammals and particularly humans will be apparent to those skilled in the art.

This invention will be more fully understood by reference to the following examples, which are intended to be illustrative of the invention, but not limiting thereof. Examples 1–6 detail the formation, and both chemical and biological testing of the liposomal amikacin formulations of the invention.

EXAMPLE 1

A lipid mixture of hydrogenated soy PC, cholesterol, and distearoyl phosphatidylglycerol was provided in a molar ratio of 2:1:0.1 respectively. The lipids were dissolved in chloroform and methanol (1: 1 by volume). The resulting solution was stirred until the lipids dissolved and a clear solution was formed. The mixing is best carried out at room temperature. A lipid film was obtained by evaporating the organic solvents under Nitrogen at room temperature.

Amikacin free base was dissolved in 10 mM phosphate buffer with 9% sucrose and the pH adjusted to 7.4 with 6.0 M HCl. The lipid film and the amikacin solution were mixed so that the concentration of the drug was about 250 mg/ml and the concentration of the lipid was about 100 mg/ml. The resulting solution was stirred and hydrated for 10–15 minutes at 65° C. The solution was sonicated for 20 minutes using a probe sonicator (Model 500 Sonic & Material). The solution was held at 65° C. for ten minutes. The solution was cooled to room temperature and centrifuged at 3600 rpm for 10 minutes. The supernatant was collected and poured through a Sephadex G-50 column to separate the liposomal formulation from the free drug. The concentration of amikacin and lipid components were determined by HPLC assay. The size was determined by optical particle sizing. The size of the liposomes varied from experiment to experiment from about 40–100 nm. For example, in one experiment a mean diameter of 62.1 nm was observed. In another, a mean diameter of 47.4 nm was observed. A preferred formulation contains a drug to lipid ratio of 1:4.

EXAMPLE 2

A lipid solution was prepared in methanol and chloroform as described in Example 1. A lipid powder was obtained in a spray drier (Yamato Pulvis Basic Unit, Model GB-21). The following settings were used: 1) pump dial at 3–4.5; 2) aspirator dial at 6; 3) pressure at 1.5–2 $Kgf/cm^2s$; 4) inlet temperature at 50° C.; and 5) outlet temperature at 40° C. The spraying took place under nitrogen for two hours. The powder was collected and combined with amikacin drug solution (as prepared in Example 1). The resulting solution was mixed for 2 minutes using a high shear mixer (Virtishear)) at 1000 rpm. The solution was placed in a beaker and set in a 40° C. water bath and hydrated with mixing until the solution reached 40° C. (about 25 minutes). The solution was then placed in a homogenizer (Gaulin 15 M) for approximately 30 passes at 10,000 psi while maintaining the inlet temperature at 40° C. The resulting solution was filtered through a 0.8 micron nylon filter. The solution was ultrafiltered to replace unencapsulated drug with new buffer. The solution was washed with 7 to 10 volumes of buffer. The resulting product was heated to 40° C. and filtered through successive 0.8, 0.45, and 0.22 micron (pore size) filters. Thus, a surprising aspect of the present invention is that the hydration of liposomes occurred significantly below the transition temperature of the formulation (about 52° C.).

EXAMPLE 3

The testing of liposome encapsulated amikacin for the treatment of MAC was performed using a murine model. Beige mice (C57B1/6bg$^j$/bg$^j$) were infected with MAC (101, type 1). The mice were infected by injection of 1×10$^7$ Colony Forming Units (cfu) in the mouse tail vein (i.v.). Three experiments were performed. In the first experiment, 40, 80 and 120 milligrams of amikacin (liposomal and free) per kilogram of mouse body-weight was given i.v. daily for 5 days, beginning 7 days after infection. The animals were sacrificed 5 days after treatment was completed and the liver, lung and spleen tissue were plated. Quantitation of organisms in liver, spleen and lung tissue was performed. The cfu were determined by growth on Middlebrook 7h11 agar plates. Untreated and empty liposomes were used as controls.

The liposomes were prepared as in Example 1. This experiment was performed in two identical parts. The liposomes in the first part were of an average size of 49.8 nm and the average size of the liposomes in the second part were 73.7 nm (mean diameter). The amikacin concentration was either 15.0 mg/ml or 13.21 mg/ml and the total lipid concentration was either 121 mg/ml or 55.7 mg/ml respectively (drug to lipid ratios: 0.123, 0.24). Free drug for all experiments was prepared in the same buffer that the liposomal formulations were contained in. The results are listed in Table 1. Table 1 lists the results for the spleen and liver tissue.

TABLE 1

Effects of Liposomal Amikacin on MAC Infected Mice Tissue

| | | Spleen | | Liver | |
|---|---|---|---|---|---|
| Regimen | # mice | cfu/g | log cfu/g | cfu/g | log cfu/g |
| untreated | 6 | 1.13 × 10$^9$ | 9.05 | 7.49 × 10$^8$ | 8.87 |
| liposomes only | 3 | 5.30 × 10$^8$ | 8.72 | 5.51 × 10$^8$ | 8.74 |
| amikacin 40 mg/kg | 5 | 4.08 × 10$^8$ | 8.61 | 1.41 × 10$^8$ | 8.15 |
| amikacin 80 mg/kg | 6 | 4.82 × 10$^8$ | 8.68 | 7.79 × 10$^7$ | 7.89 |
| amikacin 120 mg/kg | 3 | 3.46 × 10$^8$ | 8.54 | 5.65 × 10$^7$ | 7.75 |
| liposomal amikacin 40 mg/g | 6 | 5.43 × 10$^7$ | 7.73 | 1.44 × 10$^7$ | 7.16 |
| liposomal amikacin 80 mg/kg | 6 | 2.71 × 10$^7$ | 7.43 | 2.11 × 10$^7$ | 7.32 |
| liposomal amikacin 120 mg/kg | 6 | 4.03 × 10$^7$ | 7.61 | 9.86 × 10$^6$ | 6.99 |

The results for the lung study were as follows: 1) untreated regimen were 2.86×10$^7$ cfu/gram (log=7.46); 2) empty liposomes were 2.95×10$^7$ cfu/gram (log=7.47); 3) free amikacin (40 mg/kg, 80 mg/kg and 120 mg/kg) were 1.44×10$^6$ (log=6.16), 1.29×10$^6$ (log 6.11) and 9.94×10$^5$ (log=6.00) respectively; 4) liposomal amikacin (40 mg/kg, 80 mg/kg, and 120 mg/kg) were 2.28×10$^5$ (log=5.36), 3.02× 10$^5$ (log=5.48) and 4.15×10$^5$ (log=5.62).

Another experiment was carried out as above (also in two parts) except that the drug therapy was started 5 days after infection. The drug was given i.v. three times/week for 21 days. The mice were sacrificed 1–2 days after the treatment stopped. During the treatment period, a group of mice received 40 mg/Kg, 80 mg/kg, and 150 mg/kg of free amikacin and another group received 40 mg/kg, 80 mg/kg, and 160 mg/kg of liposomal amikacin. The lung tissues were not tested. Similar controls were used as above. The liposomes were prepared as described in Example 1. The average size of the liposomes was 66.5 nm or 79.6 nm (mean diameter). The concentration of the amikacin was either 15.98 mg/ml or 6.74 mg/ml. The total lipid was measure only the second part of the experiment and it was 27.0 mg/ml (drug to lipid ratio: 1:4.167). The results are listed in Table 2.

TABLE 2

Effects of Liposomal Amikacin on MAC Infected Mice Tissue

| | | Spleen | | Liver | |
|---|---|---|---|---|---|
| Regimen | # mice | cfu/g | log cfu | cfu/g | log cfu |
| untreated | 6 | 2.23 × 10$^9$ | 9.35 | 1.06 × 10$^9$ | 9.03 |
| liposomes only | 5 | 2.27 × 10$^9$ | 9.36 | 2.08 × 10$^9$ | 9.32 |
| amikacin 40 mg/kg | 6 | 5.76 × 10$^8$ | 8.76 | 1.09 × 10$^8$ | 8.04 |
| amikacin 80 mg/kg | 6 | 2.02 × 10$^8$ | 8.31 | 3.67 × 10$^7$ | 7.56 |
| amikacin 120 mg/kg | 2 | 1.48 × 10$^8$ | 8.17 | 3.15 × 10$^7$ | 7.50 |
| liposomal amikacin 40 mg/kg | 6 | 7.98 × 10$^7$ | 7.90 | 7.24 × 10$^6$ | 6.86 |
| liposomal amikacin 80 mg/kg | 4 | 2.57 × 10$^7$ | 7.41 | 2.21 × 10$^6$ | 6.34 |
| liposomal amikacin 160 mg/kg | 6 | 1.73 × 10$^7$ | 7.24 | 1.04 × 10$^6$ | 6.02 |

A third experiment was carried out as in the second experiment except that the mice treated with the liposomal amikacin received 120 mg/kg, 240 mg/kg and 320 mg/kg doses and the mice treated with the free amikacin received only 120 mg/kg doses. The liposomes were prepared as in Example 2 where the average size of the liposomes were 81.8 nm (median diameter). The amikacin concentration was 32.02 mg/ml and the total lipid concentration was 91.5 mg/ml (drug to lipid ratio: 1:2.941). The results are listed in Table 3.

TABLE 3

Effects of Liposomal Amikacin on MAC Infected Mice Tissue

| | | Spleen | | Liver | |
|---|---|---|---|---|---|
| Regimen | # mice | cfu/g | log cfu/g | cfu/g | log cfu/g |
| untreated | 6 | 3.70 × 10$^9$ | 9.57 | 1.65 × 10$^9$ | 9.22 |
| liposomes only | 6 | 4.05 × 10$^8$ | 8.61 | 1.20 × 10$^8$ | 8.08 |
| amikacin 120 mg/kg | 6 | 2.13 × 10$^8$ | 8.33 | 6.10 × 10$^7$ | 7.78 |
| liposomal amikacin 120 mg/kg | 6 | 8.8 × 10$^6$ | 6.94 | 3.67 × 10$^5$ | 5.56 |
| liposomal amikacin 240 mg/kg | 6 | 5.52 × 10$^6$ | 6.74 | 4.83 × 10$^5$ | 5.68 |
| liposomal amikacin 320 mg/kg | 6 | <3.38 × 10$^6$ | 6.53 | <2.00 × 10$^5$ | 5.30 |

The results of all the experiments establish that significantly higher doses of amikacin can be delivered without an increase in toxicity and with superior efficacy. It is known in the art that 150 mg/kg of amikacin will kill many of the mice injected. Thus, the delivery of 320 mg/kg of amikacin is a significant increase in the amount of drug delivered without lethal toxicity.

EXAMPLE 4

The efficacy and toxicity of liposomal amikacin in Pseudomonas infected mice was tested. CF-1 mice were used (females, 6–8 weeks old). The mice were obtained from Jackson Labs. A clinical isolate of *Pseudomonas aeruginosa* was obtained on a Mueller Hinton/MacConkey blood agar plate. The organisms were transferred to a Mueller Hinton plate and grown for 24 hours. Colonies were transferred to saline and grown for 48 hours. The samples were frozen in saline containing 15% fetal calf serum at $1 \times 10^8$ organisms/ml (MacFarland Standard). The colonies were stored at $-70°$ C. The colonies were thawed and grown in a Mueller Hinton plate for 24 hours. The bacteria were adjusted to $8 \times 10^6$ organisms/ml in saline containing talc (62.5 mg/ml) and 1 ml was injected intraperitoneal. A culture of inoculum on MH agar for 24 hours determined that approximately $7 \times 10^6$ cfu were delivered per mouse. Liposomal amikacin and empty liposomes were prepared as set out in Example 2. The liposomes of the amikacin formulation had an average size (median diameter) of 62.4 nanometers. The lipid concentration was 95.31 mg/ml and the amikacin concentration was 23.54 mg/ml (0.25 drug/lipid ratio). The pH of the solution containing the formulation was 7.31. The empty liposomes had an average size of 66.8 nanometers with 92.05 mg/ml of lipid. The concentration of the free amikacin solution was 23.54 mg/ml. The pH of the solution containing the liposomes was 7.33.

Mice were treated with 40 mg/kg (drug per body-weight), 80 mg/kg, 120 mg/kg and 240 mg/kg of liposomal amikacin. Mice were also treated with 40 mg/kg, 80 mg/kg, and 120 mg/kg of free amikacin. The drugs were administered intravenously in the caudal vein. Two doses were given; one at four hours after infection and one at twenty-four hours after infection. The results are listed in Table 4. The results establish that it is possible to deliver up to 240 mg/kg of amikacin using a liposome formulation with all the subjects surviving.

TABLE 4

Effects of Liposomal Amikacin on Pseudomonas Infection in Mice

| Infection | Treatment | Mortality #died/#tested hours post infection | | | | % |
|---|---|---|---|---|---|---|
| | | 24 | 30 | 48 | 72 | |
| no | none | 0/4 | 0/4 | 0/4 | | 0 |
| yes | none | 5/6 | | 6/6 | | 100 |
| yes | 40 (free amikacin) | 1/4 | 1/4 | 1/4 | 1/4 | 25 |
| yes | 80 (free amikacin) | 0/6 | 0/6 | 0/6 | 0/6 | 0 |
| yes | 120 (free amikacin) | 0/6 | 0/6 | 0/6 | 0/6 | 0 |
| yes | 40 (lipo. amikacin) | 1/4 | 3/4 | 4/4 | 4/4 | 100 |
| yes | 80 (lipo. amikacin) | 0/6 | 0/6 | 1/6 | 2/6 | 33 |
| yes | 120 (lipo. amikacin) | 0/6 | 0/6 | 0/6 | 0/6 | 0 |
| yes | 240 (lipo. amikacin) | 0/6 | 0/6 | 0/6 | 0/6 | 0 |

EXAMPLE 5

Amikacin content was measured in mouse (C57B1/6, females 2–3 months old) plasma after injection (i.v.) of free amikacin or liposomal amikacin (100 mg/kg). Liposomal amikacin was prepared as described in Example 2. Blood samples were obtained at various time intervals. The samples were collected by removing 100 microliters of blood, retroorbitally, from nonanesthetized mice. The samples were collected in heparinized capillary pipets which were plugged with modeling clay. The samples were centrifuged at 3250 rpm (20 cm rotor) for 10 minutes. The samples were analyzed using a radioimmunoassay (Diagnostic Products). The liposomal amikacin formulation contained liposomes with an average size of 43.6 nm (median diameter). The amikacin concentration was 10.09 mg/ml and the total lipid concentration was 56.8 mg/ml (drug to lipid ratio 1:5.56). The results are listed in Table 5.

TABLE 5

Amikacin Content in Mouse Plasma

| Treatment | Interval (hours) | # of mice | Average Concentration ($\mu$g/ml) | Standard deviation ($\pm\mu$g/ml) |
|---|---|---|---|---|
| Amikacin | 0.0833 | 4 | 406 | 155 |
| | 0.25 | 4 | 106 | 12 |
| | 2 | 4 | 65 | 12 |
| | 6 | 4 | none detected | |
| | 14 | | not tested | |
| | 24 | | not tested | |
| Liposomal Amikacin | 0.0833 | 4 | 530 | 258 |
| | 0.25 | 4 | 344 | 321 |
| | 2 | 3 | 346 | 199 |
| | 6 | 4 | 278 | 137 |
| | 14 | 4 | 272 | 78 |
| | 24 | 6 | 108 | 14 |

The results establish that liposomal amikacin is retained in the plasma for a significantly longer period than free amikacin.

Although this specification has been disclosed and illustrated with reference to particular applications, the principles involved are susceptible to numerous other applications which will be apparent to those skilled in the art. The invention is, therefore, to be limited only as indicated by the scope of the appended claims.

EXAMPLE 6

Liposome encapsulated amikacin was tested against both drug resistant and drug susceptible strains of *M. tuberculosis*. Liposomes were prepared as in Example 1.

Two test strains of *M. tuberculosis* were identified by the Gen-Pro (San Diego) technique. One strain was a drug resistant strain known as Vertulla. The other strain is known as H37RV. Both strains are located at the National Jewish Center for Immunology and Respiratory Medicine, Denver, Colo. For each experiment, a subculture in 7H9 broth was made from a frozen aliquot. After 1 to 2 weeks of incubation at 37° C. on a constantly rotating roller drum, the bacterial suspension for each strain was forced through a 27-gauge needle and then centrifuged at 250×g for 5 minutes to remove large clumps of bacteria. Peripheral blood from healthy purified protein derivative-negative donors was collected in a 60 ml syringe that had been pretreated with approximately 0.06 ml of a preservative-free solution containing 10,000 IU of heparin per ml (GIBCO Laboratories, Grand Island, N.Y.). This pretreated resulted in 10 IU/ml of blood. The 60 ml blood sample was placed in a tube containing a Ficoll-Hypaque gradient (Sigma Diagnostics, St. Louis, Mo.) and centrifuged at 800×g for 15 minutes at room temperature, in accordance with the manufacturer's instructions. The mononuclear cell band was collected, transferred to a 50 ml Falcon tube, and diluted with RPMI 1640 (GIBCO), containing 10 IU of heparin per ml, to a total volume of 40.0 ml. The suspension was centrifuged at 250×g for 10 minutes at room temperature. The cells were washed once in 10 ml of RPMI 1640 containing heparin and the pellet was resuspended in RPMI 1640 and adjusted to $10^7$ cells per ml. The suspension was placed in 35 mm plastic petri plates (Becton Dickinson Labware, Lincoln Park, N.J.) in two spots, 1 drop (approximately 0.05 ml) for each, resulting in monolayers containing about 5×10⁵ cells. The plates were incubated at 37° C. for 1 hour to allow the cells to adhere and were then washed twice with RPMI 1640. Then, 1.5 ml of RPMI 1640 containing 3% human autologous nonheated fresh serum was added to each plate for a 7 day period of incubation at 37° C. in the presence of 7% $CO_2$. The pH of the medium was 7.2 to 7.3.

The above-described bacterial suspension was centrifuged at 3,500×g for 30 min in a refrigerated centrifuge, and the pellet was resuspended in 2.0 ml of RPMI 1640. To estimate the number of acid-fast bacilli per milliliter of this suspension, 0.01 ml samples of the suspension were placed on Reich counting slides (Bellco Biotechnology, Vineland, N.J.) with a known number of fields (under×1,000 magnification) per circle. The slides were fixed and stained. The numbers of acid-fast bacilli per milliliter estimated from the counts on these slides proved to be accurate, as shown previously. On the basis of these counts, the bacterial suspension in RPMI 1640 was adjusted to contain $10^6$ acid-fast bacilli per ml.

After 7 days of incubation, the monocytes were considered to have matured into a macrophage monolayer. The medium was removed from the plates and replaced with the bacterial suspension at 1.5 ml per plate. After incubation for one hour, the plates were washed three times to remove the extracellular bacteria. The infected macrophages were incubated in RPMI 1640 supplemented with 1% human autologous serum. Liposomal and free amikacin was added to the cultures at the following concentrations (μg/ml of RPMI): 1, 2 and 4 for susceptible strain and 4, 8 and 16 for resistant strain. Drug free liposomes and untreated cultures were used as controls. The experiment was carried out in duplicate. The bacterial counts used in the experiment described below represented only intracellular bacteria. At days 0, 4, and 7, the medium from alternate plates was discarded, and the monolayers were lysed by exposure for 10 minutes to a 0.25% solution of sodium dodecyl sulfate at 1.0 ml per plate. After the suspension was transferred to a tube, the plate was rinsed with 1.0 ml of 7H9 broth containing 20% bovine albumin, and the rinse was then added to the same tube. Tenfold serial dilutions were made to inoculate 7H11 agar plates for subsequent colony counts. The results were expressed as the number of cfu per monolayer. The initial cfu (at day 0) is shown as measured for the liposomes only (4.3×10³). [The results of the experiment are shown in Tables 6 & 7]

TABLE 6

Activity of Amikacin (Liposomal and Free) Against Drug Resistant TB (Vertulla)

| DAYS | 0 | | 4 | | 7 | |
|---|---|---|---|---|---|---|
| | CFU (1 × 10³) | Avg. log CFU | CFU (1 × 10³) | Avg. log CFU | CFU (1 × 10³) | Avg. log CFU |
| No Treatment | | | 15, 30 | 4.4 | 500, 500 | 5.7 |
| Liposomes Only | 4.6, 4.0 | 3.6 | 10, 22 | 4.2 | 240, 360 | 5.5 |
| Liposomal Amikacin | | | | | | |
| 4 μg/ml | | | 1, 1.2 | 3.0 | 4, 3.5 | 3.6 |
| 8 μg/ml | | | 0.2, 0.5 | 2.5 | 0.28, 0.62 | 2.7 |
| 16 μg/ml | | | 0.05, 0.03 | 1.6 | 0.08, 0.09 | 1.9 |
| Amikacin | | | | | | |
| 4 μg/ml | | | 9.3, 8.0 | 3.9 | 210, 100 | 5.2 |

TABLE 6-continued

Activity of Amikacin (Liposomal and Free) Against Drug Resistant TB (Vertulla)

| DAYS | 0 | | 4 | | 7 | |
|---|---|---|---|---|---|---|
| | CFU (1 × 10³) | Avg. log CFU | CFU (1 × 10³) | Avg. log CFU | CFU (1 × 10³) | Avg. log CFU |
| 8 μg/ml | | | 5, 4 | 3.7 | 4.5, 6.2 | 3.7 |
| 16 μg/ml | | | 5, 5.4 | 3.7 | 3.7, 4.1 | 3.6 |

The results in Table 6 clearly indicate that liposomal amikacin provides an effective means for treating drug resistant *M. tuberculosis*. The level of activity against the growth of the drug resistant strain is a least about 8 times greater than free amikacin and provides activity up to at least 130 times greater than free amikacin at high doses (16 μg/ml). Liposomal amikacin at the doses studied obtained killing at each concentration, whereas the free amikacin obtained, at the most, inhibition.

TABLE 7

Activity of Amikacin (Liposomal and Free) Against Drug susceptible TB

| DAYS | 0 | | 4 | | 7 | |
|---|---|---|---|---|---|---|
| | CFU (1 × 10³) | Avg. log CFU | CFU (1 × 10³) | Avg. log CFU | CFU (1 × 10³) | Avg. log CFU |
| No Treatment | | | 110, 200 | 5.2 | 1700, 1000 | 6.1 |
| Liposomes Only | 8, 10 | 4.0 | 80, 90 | 4.9 | 1100, 1300 | 6.1 |
| Liposomal Amikacin | | | | | | |
| 1 μg/ml | | | 6, 7 | 3.8 | 100, 100 | 5.0 |
| 2 μg/ml | | | 2, 1 | 3.2 | 7.5, 8.6 | 3.9 |
| 4 μg/ml | | | 1, 1 | 3.0 | 2, 2.5 | 3.4 |
| Amikacin | | | | | | |
| 1 μg/ml | | | 50, 60 | 4.7 | 900, 800 | 5.9 |
| 2 μg/ml | | | 20, 20 | 4.3 | 40, 50 | 4.7 |
| 4 μg/ml | | | 4, 5 | 3.7 | 1.5, 3 | 3.4 |

The results in Table 7 show that liposomal amikacin is as effective or even more effective of inhibiting or killing *M. tuberculosis* at equivalent doses.

What is claimed is:

1. Liposomes comprising an encapsulated aminoglycoside wherein the liposomes are unilamellar vesicles comprised of a neutral lipid, cholesterol and a negatively charged lipid and having an average size of less than 100 nm which are stable in liquid form for at least 2 weeks at 22° C. without significant change in size or loss of more than 10% of the encapsulated aminoglycoside wherein the negatively charged lipid is less than 20% total lipid.

2. A composition for treating a bacterial infection in a patient comprising an aminoglycoside encapsulated in liposomes, wherein the liposomes are comprised of a cholesterol, a neutral lipid and a negatively charged lipid, wherein said negatively charged lipid is less than 20% of the total lipid and wherein the liposomes consist of unilamellar vesicles having an average size of less than 100 nm.

3. The composition of claim 2 wherein the negatively charged lipid is 5% or less of the total lipid.

4. The composition of claim 2 wherein the neutral lipid, cholesterol and negatively charged lipid are in a molar ratio of about 2:1:0.1.

5. The composition of claim 2 wherein the aminoglycoside to total lipid molar ratio is from 1:9 to 1:3.

6. The composition of claim 2 wherein the neutral and negatively charged lipids are saturated.

7. The composition of claim 6 wherein the saturated neutral lipid is selected from the group consisting of hydrogenated egg phosphatidylcholine (HEPC), dimyristoylphosphatidylcholine (DMPC), hydrogenated soy phosphatidylcholine (HSPC), distearoyl phosphatidylcholine (DSPC), and dipalmitoyl phosphatidylcholine (DPPC).

8. The composition of claim 6 wherein the saturated negatively charged lipid is selected from the group consisting of hydrogenated soy phosphatidylglycerol (HSPG), hydrogenated egg phosphatidylglycerol (HEPG), distearoylphosphatidylglycerol (DSPG), dimyristoyl phosphatidylglycerol (DMPG), and dilaurylphosphatidylglycerol (DLPG).

9. The composition of claim 2 wherein said aminoglycoside is selected from the group consisting of streptomycin, neomycin, kanamycin, gentamicin, tobramycin, sisomicin, amikacin, and netilmicin.

10. A composition for inhibiting bacterial growth in a patient comprising an aminoglycoside encapsulated in liposomes, wherein the liposomes are comprised of a cholesterol, a neutral lipid and a negatively charged lipid, wherein the negatively charged lipid is less than 20% of the total lipid and wherein said liposomes consist of unilamellar vesicles having an average size of less than 100 nm.

11. A method of treating a bacterial infection in a patient comprising the delivery to the patient of an effective amount of liposomes comprising an encapsulated aminoglycoside, wherein the liposomes are comprised of a cholesterol, a neutral lipid and a negatively charged lipid, wherein said negatively charged lipid is less than 20% of the total lipid and wherein the liposomes consist of unilamellar vesicles having an average size of less than 100 nm.

12. The method of claim 11 wherein the negatively charged lipid is 5% or less of the total lipid.

13. The method of claim 11 wherein the neutral lipid, cholesterol and negatively charged lipid are in a molar ratio of about 2:1:0.1.

14. The method of claim 11 wherein the aminoglycoside to total lipid molar ratio is from 1:9 to 1:3.

15. The method of claim 11 wherein the neutral and negatively charged lipids are saturated.

16. The method of claim 15 wherein the saturated neutral lipid is selected from the group consisting of hydrogenated egg phosphatidylcholine (HEPC), dimyristoylphosphatidylcholine (DMPC), hydrogenated soy phosphatidylcholine (HSPC), distearoyl phosphatidylcholine (DSPC), and dipalmitoyl phosphatidylcholine (DPPC).

17. The method of claim 15 wherein the saturated negatively charged lipid is selected from the group consisting of hydrogenated soy phosphatidylglycerol (HSPG), hydrogenated egg phosphatidylglycerol (HEPG), distearoylphosphatidylglycerol (DSPG), dimyristoyl phosphatidylglycerol (DMPG), and dilaurylphosphatidylglycerol (DLPG).

18. The method of claim 11 wherein said aminoglycoside is selected from the group consisting of streptomycin, neomycin, kanamycin, gentamicin, tobramycin, sisomicin, amikacin, and netilmicin.

19. A method of inhibiting bacterial growth in a patient comprising the delivery to the patient of an effective amount of liposomes comprising an encapsulated aminoglycoside, wherein the liposomes are comprised of a cholesterol, a neutral lipid and a negatively charged lipid, wherein the negatively charged lipid is less than 20% of the total lipid and wherein said liposomes consist of unilamellar vesicles having an average size of less than 100 nm.

20. A method of making liposomes comprising an encapsulated aminoglycoside, said method comprising:
   a) forming a lipid powder comprised of a cholesterol, a neutral lipid, and a negatively charged lipid, wherein the negatively charged lipid is less than 20% of the total lipid;
   b) mixing the powder with an aminoglycoside;
   c) hydrating the mixture whereby the aminoglycoside becomes encapsulated; and
   d) applying a shearing force whereby liposomes consisting of unilamellar vesicles having an average size of less than 100 nm are obtained.

21. The method of claim 20 wherein the negatively charged lipid is 5% or less of the total lipid.

22. The method of claim 20 wherein the neutral lipid, cholesterol and negatively charged lipid are in a molar ratio of about 2:1:0.1.

23. The method of claim 20 wherein the neutral and negatively charged lipids are saturated.

24. The method of claim 23 wherein the saturated neutral lipid is selected from the group consisting of hydrogenated egg phosphatidylcholine (HEPC), dimyristoylphosphatidylcholine (DMPC), hydrogenated soy phosphatidylcholine (HSPC), distearoyl phosphatidylcholine (DSPC), and dipalmitoyl phosphatidylcholine (DPPC).

25. The method of claim 23 wherein the saturated negatively charged lipid is selected from the group consisting of hydrogenated soy phosphatidylglycerol (HSPG), hydrogenated egg phosphatidylglycerol (HEPG), distearoylphosphatidylglycerol (DSPG), dimyristoyl phosphatidylglycerol (DMPG), and dilaurylphosphatidylglycerol (DLPG).

26. The method of claim 20 wherein said aminoglycoside is selected from the group consisting of streptomycin, neomycin, kanamycin, gentamicin, tobramycin, sisomicin, amikacin, and netilmicin.

* * * * *